United States Patent [19]

Tretinyak

[11] Patent Number: 4,630,616
[45] Date of Patent: Dec. 23, 1986

[54] BONE MARROW NEEDLE
[75] Inventor: Carl W. Tretinyak, Rochester, Minn.
[73] Assignee: Berkley and Company, Inc., Spirit Lake, Iowa
[21] Appl. No.: 766,681
[22] Filed: Aug. 19, 1985

Related U.S. Application Data

[63] Continuation of Ser. No. 621,135, Jun. 15, 1984, abandoned, which is a continuation of Ser. No. 225,048, Apr. 17, 1981, abandoned.

[51] Int. Cl.⁴ .............................................. A61B 10/00
[52] U.S. Cl. ..................................... 128/753; 128/754; 604/165
[58] Field of Search ............................... 128/749–755, 128/347, 214.4; 604/164, 165

[56] References Cited

U.S. PATENT DOCUMENTS

| 3,001,522 | 9/1961 | Silverman | 128/754 |
|---|---|---|---|
| 4,013,080 | 3/1977 | Froning | 128/347 |
| 4,141,365 | 2/1979 | Fischell et al. | 128/347 X |
| 4,256,119 | 3/1981 | Gauthier | 128/754 |
| 4,262,676 | 4/1981 | Jamshidi | 128/754 X |
| 4,308,875 | 1/1982 | Young | 128/753 |
| 4,314,565 | 2/1982 | Lee | 128/753 |
| 4,326,519 | 4/1982 | D'Alo et al. | 128/214.4 |

Primary Examiner—Kyle L. Howell
Assistant Examiner—John C. Hanley
Attorney, Agent, or Firm—Faegre & Benson

[57] ABSTRACT

A bone marrow needle has a cannula (12) connected to a cannula handle portion (18) extending equal distances from the axis of the cannula bore. A stylet (14) is slidably positioned into the cannula with its stylet handle (16) matingly receiving the proximal projections (18.4, 18.5) of the cannula handle portion into recess (16.6), thus preventing relative rotational movement of the cannula and stylus during use. Proximal projections (18.4, 18.5) define a space therebetween for a syringe connector (12.3) that enables aspiration through the cannula after insertion into the bone.

2 Claims, 8 Drawing Figures

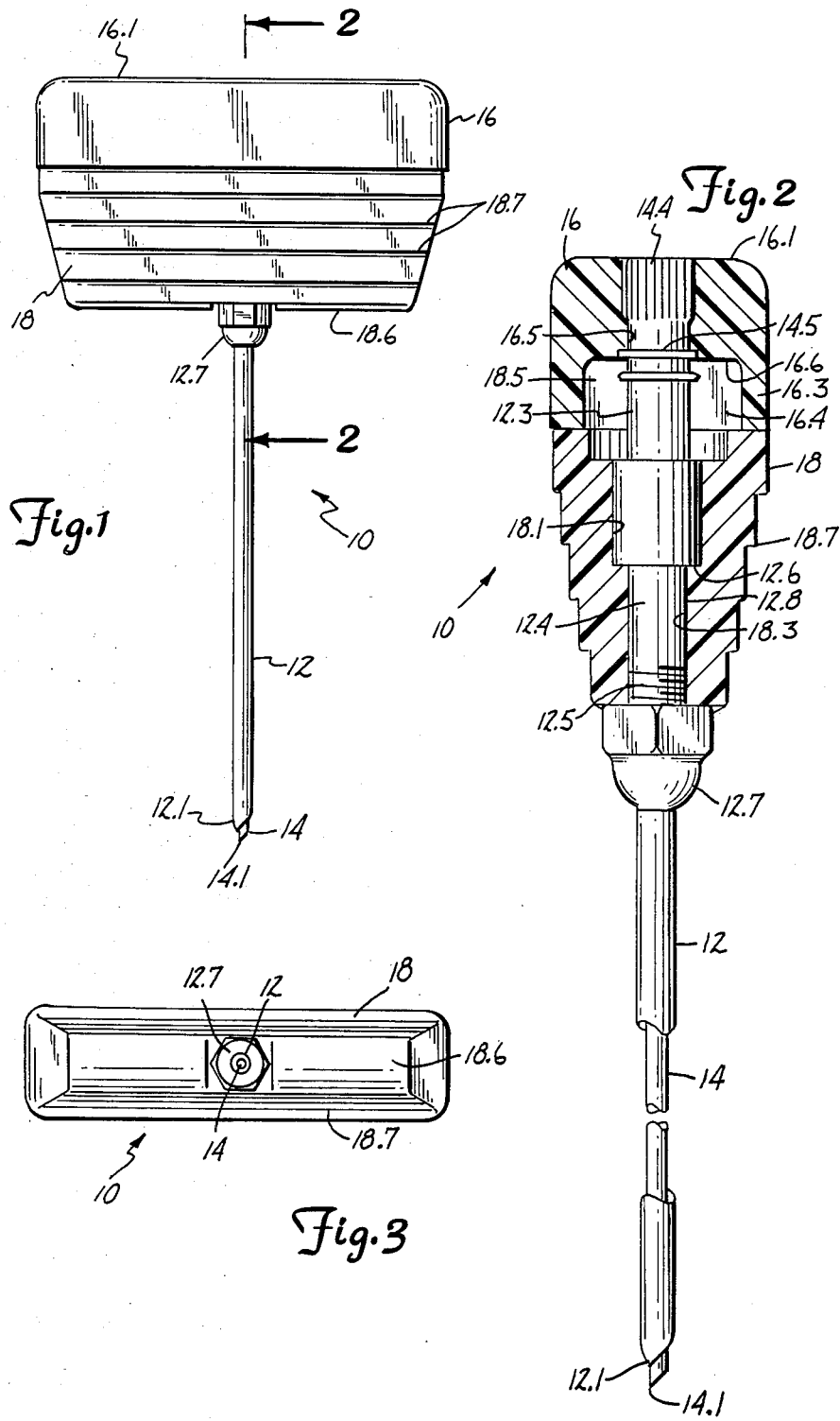

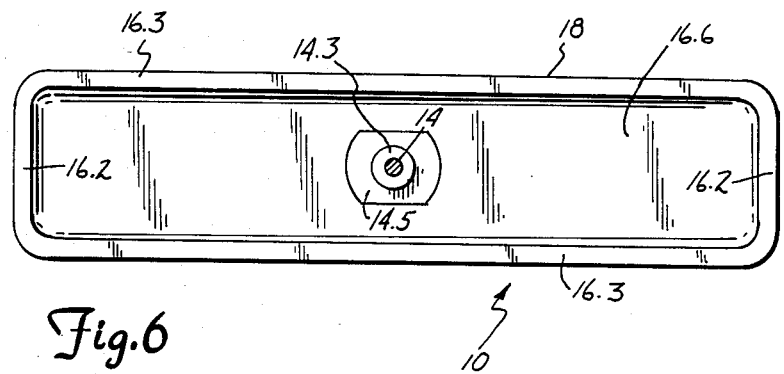
Fig.6
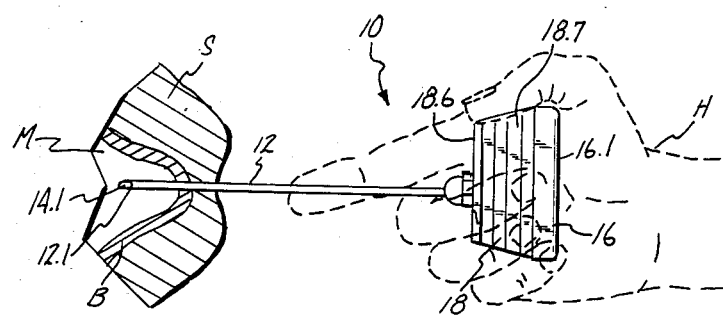
Fig.7
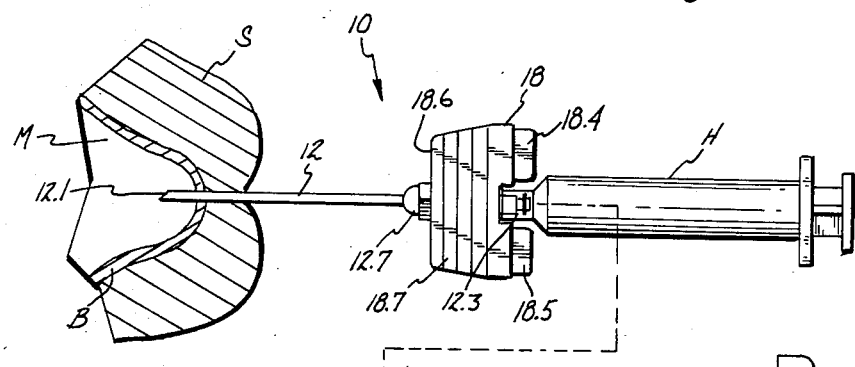
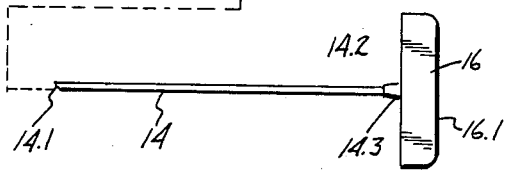
Fig.8

BONE MARROW NEEDLE

This is a continuation of application Ser. No. 621,135, filed June 15, 1984, now abandoned which was a continuation of Ser. No. 225,048, filed Apr. 17, 1981, now abandoned.

TECHNICAL FIELD

The invention relates to medical instruments, and particularly to instruments employed to withdraw bone marrow from bones in biopsy and transplant procedures.

BACKGROUND ART

In the field of medicine, it is often desirable to obtain small samples of body substances such as bone marrow for diagnostic purposes, and to withdraw somewhat larger portions of bone marrow for bone marrow transplant procedures. The latter may have particular importance in the treatment of certain blood disorders, such as leukemia.

The outer layer of marrow-containing bones is very hard, and considerable force must be employed to force a sharpened stylet or the like through this layer and into the marrow-containing cavity. The surgeon must exercise not only considerable strength, but also great care, to avoid slipping of the stylet on the bony surface and to properly position and orient the stylet so that the bone marrow cavity is reached.

On prior biopsy needle, shown in U.S. Pat. No. 3,628,524, included a hollow cannula and a stylet received in the cannula. The stylet terminated proximally in a head spaced proximally of the open end of the cannula, and was held to the cannula by means of a pin and slot arrangement. Small grips extended outwardly from either side of the cannula at its proximal end. In use, a surgeon would place a gauze sponge or the like in his palm, and the head of the stylet then would be pressed into the sponge, the surgeon grasping as he could the device with the index finger extending, for guidance, along the cannula.

In another device, the cannula itself was provided with a palm-contacting handle, the stylet terminating proximally in a palm-contacting surface substantially co-extensive with the handle so that distal force could be applied against both the cannula and the stylet. In this embodiment, the stylet and handle were locked together so that distal forces applied to the cannula alone were transmitted as well to the stylet.

Surgeons have found it difficult to grasp such bone marrow needles as are shown in U.S. Pat. No. 3,628,524 so that sufficient axial and rotative forces could be applied to drive the stylet through the hard, outer layer of a marrow-containing bone and yet precisely control the orientation of the stylet and the cannula of such needles. At times, it has been necessary to use a mallet to drive the sharpened stylet through the hard outer bone layer. With the device described above having a palm-contacting handle attached to the cannula, it is necessary to have a firm, yet releasable lock between the cannula and stylet so that movement of the cannula will result in coordinate movement of the stylet as well, such construction contributing to the cost of the needle.

DISCLOSURE OF THE INVENTION

The present invention provides a needle for withdrawing bone marrow, the needle having a cannula with proximal and distal ends and a stylet with proximal and distal ends that is slideably received coaxially in the cannula. The needle is characterized by including a handle rigidly attached to the proximal end of the stylet, the handle having a broad, distallyfacing, palm-contacting surface extending generally normally of the axis of the stylet and engageable with the palm of the user to permit significant axial and rotative forces to be applied distally upon the stylet to force the latter through bone. The needle is further characterized by handle-receiving means carried by the proximal end of the cannula for releasably receiving the handle and for preventing rotation of the handle about the axis of the stylet when the handle is received by the handle-receiving means. The handlereceiving means includes means providing a clear passageway for a syringe or the like to attach to the proximal end of the cannula upon removal of the stylet. In a preferred embodiment, the stylet terminates distally in a syringe connector, and the handle and handle receiving means cooperate to protectably enclose the syringe connector.

BRIEF DESCRIPTION OF THE DRAWING

FIG. 1 is a plan view of a bone marrow needle of the invention;

FIG. 2 is a cross-sectional, partially broken away view taken along line 2—2 of FIG. 1;

FIG. 3 is a bottom view of the device shown in FIG. 1;

FIG. 6 is a cross-sectional view taken along line 6—6 of FIG. 1;

FIG. 7 is a diagramatic view showing one step in the biopsy or bone marrow transplant procedure; and FIG. 8 is a diagramtic view showing another step in a bone marrow transplant or biopsy procedure.

BEST MODE FOR CARRYING OUT THE INVENTION

Figure 5:
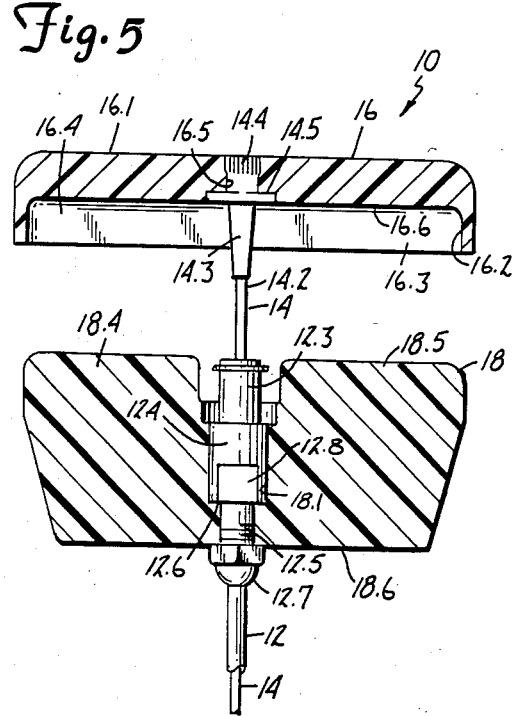
FIG. 5 is a broken-away, cross-sectional view taken along line 5—5 of FIG. 4.

The bone marrow needle of the invention is typified generally as (10) and comprises a cannula (12) within which is slideably received a stylet (14), the latter having a sharpened distal end (14.1). At its proximal end, the stylet (14) is provided with a broad, palm-fitting handle (16). The distal end (12.1) of the cannula is provided with a sharpened edge, and at least the outer surface of the cannula is tapered inwardly near its distal end as shown best in FIG. 2. The inner surface (not shown) of the cannula (12) near its distal end (12.1) preferably also is tapered inwardly. The distal end (12.1) of the cannula desirably fits snugly but slideably about the distal end portion of the stylet so as to avoid sharp shoulders which might hinder the entrance of the stylet and cannula into a bone. At its proximal end (12.2), the cannula (12) is provided with a syringe attachment, typified by the female leur lock fitting (12.3) and also handle receiving means illustrated at (18) for receiving the handle (16) when the stylet (14) has been moved distally in the cannula (12).

The handle (16) is provided with a proximally facing, broad, palm-contacting surface that extends generally normally from the axis of the stylet and which, as shown in FIG. 7, is received easily and snugly in the palm of a surgeon. The handle preferably is shaped such that the palm-contacting surface (16.1) forms a broad, elongated surface extending normally outwardly from either side of the axis of the stylet (14), but it will be understood that other broad, palm-contacting surface shapes can be employed as well. At its proximal end (14.2), the stylet (14), which commonly is made of stainless steel, is received within a tapered hub (14.3) terminating proximally in a splined shaft (14.4). A small, generally rectangular plate (14.5), extending in a plane generally normal to the axis of the stylet, is provided at the proximal end of the hub. The handle (16) is provided with peripheral, proximally extending end and side walls (16.2, 16.3) defining a distally open recess (16.4). Through the thickness of the handle (16) is formed a central aperture (16.5) sized to receive the splined shaft (14.4) in a press fit, the plate (14.5) of the stylet being received in an appropriately sized recess formed in the distally facing wall (16.6) of the handle. The plate (14.5), as depicted, prevents the stylet from escaping proximally through the orifice in the handle, and because of its non-circular (preferably rectangular) orientation, the plate (14.5) also prevents the stylet from rotating about its axis with respect to the handle. The handle (16) is itself preferably formed from a plastic such as an acetal resin (e.g., the product sold under the trade name "Delrin" by E. I. Dupont de Nemours & Co., Inc.,) a polycarbonate (e.g., the product sold under the trade name "Lexan" by the General Electric Company), and the like. The press fit between the splined shaft (14.4) and the handle orifice (16.5) is sufficient to securely anchor the stylet to the handle.

The cannula (12) preferably terminates in an enlarged, hollow hub (12.4) having a threaded distal end (12.5). An orifice (18.1) is formed through the thickness of the handle-receiving means (18) and is aligned with the orifice in the handle when the latter is received by the handle-receiving means. The hub (12.4) has a distally-facing shoulder (12.6) that engages the proximally facing shoulder formed in the orifice (18.2) of the handle-receiving means, the threaded distal end (12.5) of the hub extending through the orifice (18.1). A threaded nut (12.7) is then exteriorly threaded upon the protruding threaded end (12.5) of the hub to draw the shoulders (12.6, 18.2) together tightly and to thus lock the cannula (12) to the handle-receiving means. The hub (12.4) includes an exterior, flattened surface (12.8) that is received in facing engagement with the flat, inner surface (18.3) of the orifice in the handle-receiving means, thereby preventing respective rotation between the hub and handle-receiving means.

Figure 4:
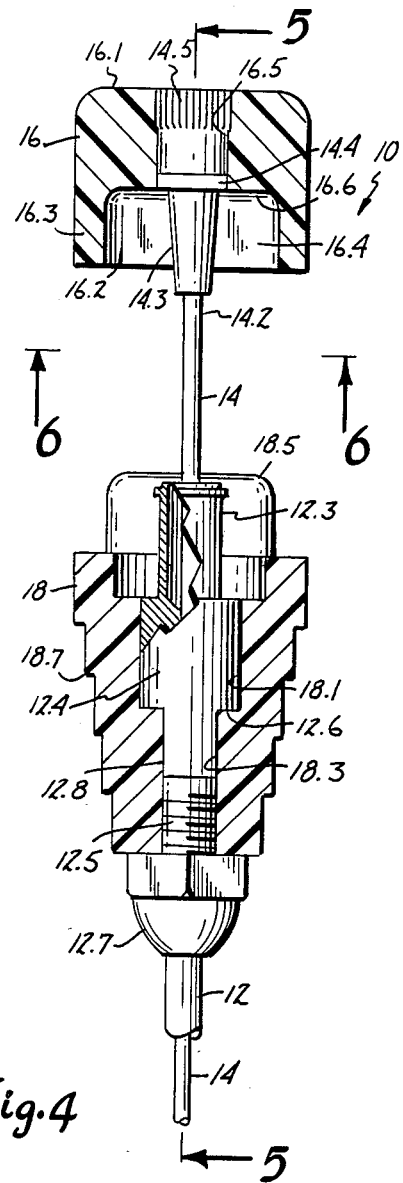
FIG. 4 is a view similar to that of FIG. 2 but showing the cannula and stylet portions partially disassembled.

Smoothly rounded projections (18.4, 18.5) arise proximally from the handle-receiving means (18), the projections being shaped so as to be received within the distally-open recess (16.4) of the handle (16) such that when the handle has been received by the handle-receiving means, the projections (18.4, 18.5) make contact with inner surfaces of the walls (16.2, 16.3) and floor (16.6) of the handle recess (16.4) thereby releasably locking the handle and handle-receiving means together and preventing the handle from rotating with respect to the handle-receiving means. As shown perhaps best in FIGS. 4 and 5, the projections (18.4, 18.5) shelter between them a leur lock fitting (12.3) so that even when the stylet and handle have been removed, the leur lock fitting is prevented from contacting the planar surface upon whihc the cannula may be surface upon which the cannula placed, thereby avoiding damage to and restraining contamination of the leur lock fitting (12.3). Moreover, when the handle has been received by the handle-receiving means, the side walls (16.3) and floor (16.6) of the handle surround and overlie the leur lock fitting (12.3), the handle and handle-receiving means thus cooperating to protectively enclose the syringe connector.

The handle-receiving means (18) preferably is provided with generally distally facing, finger-gripping surfaces (18.6), and the handle-receiving means, or the handle, or both, may be provided with roughened outer surfaces typified by the stair-step serrations or corrugations shown best in FIGS. 1 and 2.

When the handle (16) has been received by the handle-receiving means (18), the tapered hub (14.3) is received, preferably loosely, within the interior of the leur lock fitting (12.3). The relative lengths of the stylet (14) and cannula (12) are such that the sharpened distal end (14.1) of the stylet protrudes for a short distance beyond the sharpened, distal end (12.1) of the cannula. The projections (18.4, 18.5) desirably snugly but slideably fit within the recess (16.4) of the handle so that when the handle is received by the handle-receiving means, as depicted in FIGS. 1 and 2, the slight friction therebetween will maintain the handle in position but permit it to be pulled proximally of the handle-receiving means with only very slight effort. As depicted in the drawing, the confronting surfaces of the handle (16) and handle-receiving means (18) are so configured as to enable them to axially nest together to form a unitary composite grip for a surgeon, the palm-contacting surface (16.1) being received comfortable in the surgeon's palm with the surgeon's fingers gripping outer surfaces of the handle-receiving means. The mating projections (18.4), (18.5) spaced from the axis of the needle and the recesses (16.4) prevent relative rotation between the handle and stylet-receiving means. Yet, the handle (16) may be freely axially withdrawn from the handle-receiving means as needed during a surgical procedure.

FIGS. 7 and 8 relate to the actual use of the bone marrow needle of the invention. The skin and fatty tissues and the like of a patient are designated generally as "S", the hard, bony layer of a bone is designated "B", and the marrow-containing interior of the bone is designated "M". Referring to FIG. 7, the needle of the invention is gripped firmly by the hand (shown as "H" in phantom lines in FIG. 7), the broad, palm-contacting surface (16.1) of the handle being firmly received in the palm of the surgeon and the fingers being wrapped about the finger-gripping surface (18.6) of the handle-receiving means. It is common for a surgeon to place his index finger along the length of the cannula, as shown, for greater control during the bone-piercing operation. The thumb may be wrapped over the sides of the handle and handle-receiving means for greater control and leverage. The sharpened stylet and cannula are inserted through the skin and fatty layers "S" until the outer surface of the bony layer "b" is encountered, following which the surgeon exerts significant distal and rotative forces on the handle, in a controlled manner, to cause the sharpened end of the stylet to pierce the bony layer "B", the distal ends of the stylet and cannula penetrating into the marrow cavity "M" (FIG. 7). It will be noted that the handle (16), rigidly attached to the stylet (14), bears the brunt of the force applied by the surgeon, the cannula following the stylet in a preferred embodiment in response to the transmission of axial and rotary forces from the handle to the handle-receiving means. The palm-contacting surface of the handle, as noted above, is elongated in generally a direction normal to the axis of the stylet, and hence the portions of the handle that project laterally outwardly from the axis of the stylet function as levers enabling the surgeon to apply considerable torque to the stylet.

Once the distal ends of the stylet and cannula have pierced the hard bony layer "B" and have penetrated into the marrow cavity "m", the stylet is removed from the cannula by gently pulling the handle proximally while holding the cannula in place. In a preferred embodiment, the handle is readily removed proximally, that is, axially outwardly, of the handle-receiving means by very gentle manual force, thereby avoiding any twisting, unlocking motion that might cause the cannula to rock back and forth in the hole pierced through the bony layer "B". By thus removing the handle and stylet, the leur lock or similar fitting (12.3) disposed at the proximal end of the cannula is exposed and to it is attached a hypodermic syringe (designated "H" in FIG. 7). Withdrawal of the plunger of the hypodermic needle causes bone marrow to be drawn into the syringe for later examination or for transplantation into another patient. When sufficient bone marrow has been drawn into the cannula, the cannula, handle-receiving means and hypodermic syringe may be withdrawn as a unit, and the contents of the cannula may be then expelled as desired.

In a preferred embodiment, the handle (16) preferably proximally overlays substantially the entire handle-receiving means, and hence substantially the entire axial force generated by the surgeon's palm is transmitted axially to the stylet. Further, the handle and handle-receiving means preferably cooperate to protectively enclose the hypodermic syringe fitting (12.3) at the proximal end of the cannula to reduce the likelihood of contamination of that fitting. Further, the palm-contacting surface of the handle is desirably elongated in a direction generally normal to the axis of the stylet. In a preferred embodiment, the handle and handle-receiving means are provided with confronting projections and recesses receiving the projections so that the handle is restrained from rotation with respect to the handle-receiving means but can readily be removed axially and proximally from the handle-receiving means with only gentle manual effort. The needle of the invention can be used by either hand of the surgeon and can be rotated in either direction about its axis without fear of accidentally dislodging the handle from the handle-receiving means. Further, the axial and rotative forces exerted by a surgeon upon the handle are transmitted to the cannula by the engagement between the handle and the handle-receiving means; in the preferred embodiment, there is no force-transmitting connection between the hypodermic syringe fitting (12.3) and the stylet, thereby avoiding the possibility of damage to the hypodermic syringe fitting.

Various adaptations and modifications of the invention will be suggested to those skilled in the art. For example, although the handle-receiving means is depicted as having a substantial axial dimension with respect to the cannula, this dimension can be reduced considerably if desired since the primary force exerted by the surgeon is upon the handle which in turn forces the stylet through the hard bony layer "B" of a marrow-containing bone. Because of the close, tapered fit of the distal end of the cannula about the distal end of the stylet, the amount of axial force that must be placed on the cannula to force it through the perforation made by the stylet is small in comparison to the axial force imparted to the distal end of the stylet.

While a preferred embodiment of the invention has been described, it should be understood that various changes, adaptations and modifications may be made therein without departing from the spirit of the invention and the scope of the appended claims.

What is claimed is:

1. A bone marrow biopsy needle assembly, comprising:
   (a) an elongated tubular cannula having an axially extending bore therethrough;
   (b) a cannula handle positioned on the proximal end of said cannula; wherein
   (c) said cannula handle extends perpendicularly to the axis of said cannula; and wherein
   (d) said cannula handle is comprised of two equal rectangular halves extending in diametrically opposed directions to each other from said cannula axis;
   (e) each of said equal halves of said cannula handle having proximally extending shoulder projections substantially parallel to the axis;
   (f) an orifice in said cannula handle in flow communication with said cannula bore, said orifice being coaxial with said cannula bore;
   (g) a stylus handle removably positioned on the proximal end of said cannula handle; wherein
   (h) said stylus handle extends perpendicularly to the axis of said cannula and includes an elongated palm contacting surface on the proximal side thereof; and wherein
   (i) said stylus handle is comprised of two equal rectangular halves extending in diametrically opposed directions to each other from said cannula axis along the same diameter and substantially to the same extent as said equal halves of said cannula handle;
   (j) an elongated stylus extending from the distal side of said stylus handle and slidably received within said cannula bore, said stylus having a sharpened distal tip which extends distally from the distal end of said cannula;
   (k) and wherein the distal side of said stylus handle further includes recess means mated to the shouldered projections for allowing relative movement between the stylus and cannula handles only in the axial direction of siad cannula;
   (l) whereby when said equal cannula handle halves are received in said recesses of said equal stylus handle halves, force may be rotatingly applied around either axial direction of said elongated stylet positioned in said elongated cannula without relative rotation of said elongated stylet and said elongated cannula.

2. The assembly of claim 1, further comprising:
   (a) a recess on the proximal side and defined by said shoulder projections of said cannular handle which is coaxial with said orifice;
   (b) a hypodermic syringe fitting proximally extending from said cannula handle in said recess to an extent no more than the proximal extent of the shoulders from said cannula handle; and wherein
   (c) said hypodermic syringe fitting is in flow communication with said orifice; and
   (d) said stylus handle further includes a means on the distal side for covering the proximal end of the syringe fitting when said recess means and shoulder projections are mated.

* * * * *